(12) United States Patent
Barbee et al.

(10) Patent No.: US 10,144,015 B2
(45) Date of Patent: Dec. 4, 2018

(54) ROTOR PLATE AND BUCKET ASSEMBLY AND METHOD FOR USING SAME

(71) Applicant: LIFE TECHNOLOGIES CORPORATION, Carlsbad, CA (US)

(72) Inventors: Kristopher Barbee, East Haven, CT (US); Rui Zheng, North Brandford, CT (US); Sean McCusker, New Haven, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 544 days.

(21) Appl. No.: 14/536,489

(22) Filed: Nov. 7, 2014

(65) Prior Publication Data

US 2015/0133283 A1   May 14, 2015

Related U.S. Application Data

(60) Provisional application No. 61/934,271, filed on Jan. 31, 2014, provisional application No. 61/902,724, filed on Nov. 11, 2013.

(51) Int. Cl.
*B04B 7/08* (2006.01)
*B01D 21/26* (2006.01)
(Continued)

(52) U.S. Cl.
CPC .............. *B04B 7/08* (2013.01); *B01D 21/262* (2013.01); *B04B 5/0421* (2013.01);
(Continued)

(58) Field of Classification Search
CPC ....... B01D 21/262; B04B 7/08; B04B 5/0421; B04B 2011/046; G01N 2035/0449; G01N 2035/00158; G01N 2035/00495
(Continued)

(56) References Cited

U.S. PATENT DOCUMENTS 3,951,334 A * 4/1976 Fleming ................ B04B 5/0421
494/20
5,045,047 A * 9/1991 Hutchins ................... B04B 5/02
494/17
(Continued)

FOREIGN PATENT DOCUMENTS

DE          3512848          10/1985
DE          3512848 A1 *    10/1985    ........... B04B 5/0421
(Continued)

OTHER PUBLICATIONS

Birren, et al., "Genome Analysis Laboratory Manual Series", *B. Birren, ed., Cold Spring Harbor Laboratory Press*, vols. 1-4,, 1997-1999.
(Continued)

*Primary Examiner* — Walter D. Griffin
*Assistant Examiner* — Shuyi S. Liu

(57) ABSTRACT

A rotor assembly includes a rotor plate to rotate around a first axis; a bucket rotatably attached to the rotor plate and to rotate around a second axis; and a stop plate to rotate around the first axis relative to the rotor plate between an open position and a closed position, when in the closed position, the stop plate is to engage the bucket to fix an angular position of the bucket relative to a plane of rotation of the rotor assembly.

6 Claims, 13 Drawing Sheets

(51) Int. Cl.
*B04B 5/04* (2006.01)
*B04B 11/04* (2006.01)
*G01N 35/00* (2006.01)
*G01N 35/04* (2006.01)

(52) U.S. Cl.
CPC .......... *B04B 2011/046* (2013.01); *G01N 2035/00158* (2013.01); *G01N 2035/00495* (2013.01); *G01N 2035/0449* (2013.01)

(58) Field of Classification Search
USPC .......................................... 494/37, 43, 46
See application file for complete search history.

(56) References Cited

U.S. PATENT DOCUMENTS

| | | | |
|---|---|---|---|
| 5,578,269 A * | 11/1996 | Yaremko | G01N 35/025 210/361 |
| 5,707,331 A * | 1/1998 | Wells | B04B 9/14 494/20 |
| 5,733,572 A | 3/1998 | Unger et al. | |
| 6,151,969 A * | 11/2000 | Miller | G01N 17/02 324/71.1 |
| 6,156,501 A | 12/2000 | McGall et al. | |
| 6,238,862 B1 | 5/2001 | McGall et al. | |
| 6,306,643 B1 | 10/2001 | Gentalen et al. | |
| 6,309,823 B1 | 10/2001 | Cronin et al. | |
| 6,429,027 B1 | 8/2002 | Chee et al. | |
| 6,544,732 B1 | 4/2003 | Chee et al. | |
| 6,576,425 B2 | 6/2003 | McGall et al. | |
| 6,620,584 B1 | 9/2003 | Chee et al. | |
| 6,705,754 B2 | 3/2004 | Winkler et al. | |
| 6,852,490 B2 | 2/2005 | Gentalen et al. | |
| 6,858,394 B1 | 2/2005 | Chee et al. | |
| 6,890,741 B2 | 5/2005 | Fan et al. | |
| 6,942,968 B1 | 9/2005 | Dickinson et al. | |
| 6,998,274 B2 | 2/2006 | Chee et al. | |
| 7,033,754 B2 | 4/2006 | Chee et al. | |
| 7,060,431 B2 | 6/2006 | Chee et al. | |
| 7,060,443 B2 | 6/2006 | McGall et al. | |
| 7,115,364 B1 | 10/2006 | Chee et al. | |
| 7,226,734 B2 | 6/2007 | Chee et al. | |
| 7,455,971 B2 | 11/2008 | Chee et al. | |
| 7,510,841 B2 | 3/2009 | Stuelpnagel et al. | |
| 7,563,576 B2 | 7/2009 | Chee et al. | |
| 7,582,420 B2 | 9/2009 | Oliphant et al. | |
| 7,612,020 B2 | 11/2009 | Stuelpnagel et al. | |
| 7,781,226 B2 | 8/2010 | McDevitt et al. | |
| 7,794,943 B2 | 9/2010 | McGall et al. | |
| 7,846,659 B2 | 12/2010 | Cronin et al. | |
| 7,901,897 B2 | 3/2011 | Stuelpnagel et al. | |
| 7,955,794 B2 | 6/2011 | Shen et al. | |
| 7,960,119 B2 | 6/2011 | Chee et al. | |
| 8,003,354 B2 | 8/2011 | Shen et al. | |
| 8,206,917 B2 | 6/2012 | Chee et al. | |
| 8,460,865 B2 | 6/2013 | Chee et al. | |
| 8,481,268 B2 | 7/2013 | Chee et al. | |
| 8,486,625 B2 | 7/2013 | Gunderson et al. | |
| 8,563,246 B2 | 10/2013 | Chee et al. | |
| 8,574,835 B2 | 11/2013 | Hinz et al. | |
| 8,586,312 B2 | 11/2013 | Gentalen et al. | |
| 8,628,952 B2 | 1/2014 | Stuelpnagel et al. | |
| 8,669,053 B2 | 3/2014 | Stuelpnagel et al. | |
| 8,795,967 B2 | 8/2014 | Chee et al. | |
| 2002/0001803 A1 | 1/2002 | Smith et al. | |
| 2004/0141880 A1 | 7/2004 | Handler et al. | |
| 2005/0191620 A1 | 9/2005 | McDevitt et al. | |
| 2006/0234267 A1 | 10/2006 | Besemer et al. | |
| 2006/0257941 A1 | 11/2006 | McDevitt et al. | |
| 2009/0026082 A1 | 1/2009 | Rothberg et al. | |
| 2009/0127589 A1 | 5/2009 | Rothberg et al. | |
| 2010/0137143 A1 | 6/2010 | Rothberg et al. | |
| 2010/0197507 A1 | 8/2010 | Rothberg et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2014/0100122 A1 | 4/2014 | Rearick et al. | |
| 2014/0179505 A1 * | 6/2014 | David | B04B 5/0421 494/20 |
| 2015/0031558 A1 | 1/2015 | Rearick et al. | |

FOREIGN PATENT DOCUMENTS

| | | |
|---|---|---|
| WO | 1997/40942 | 11/1997 |
| WO | 2005012549 | 2/2005 |
| WO | 2005085855 | 9/2005 |
| WO | 2012145574 | 10/2012 |

OTHER PUBLICATIONS

Diffenbach, et al., "PCR Primer, A Laboratory Manual", *Cold Spring Harbor Press*, 1995, 1995.
Hermanson, Greg, "Bio", *Second Edition, Academic Press*, 1202 pages, Part 8 of 12, 2008, pp. 668-769.
Hermanson, Greg, "Bioconjugate Techniques", *Second Edition, Academic Press*, 1202 pages, Part 10 of 12, 2008, pp. 872-973.
Hermanson, Greg, "Bioconjugate Techniques", *Second Edition, Academic Press*, 1202 pages, Part 11 of 12, 2008, pp. 974-1075.
Hermanson, Greg, "Bioconjugate Techniques", *Second Edition, Academic Press*, 1202 pages, Part 12 of 12, 2008, pp. 1076-1202.
Hermanson, Greg, "Bioconjugate Techniques", *Second Edition, Academic Press*, 1202 pages, Part 2 of 12, 2008, pp. 106-157.
Hermanson, Greg, "Bioconjugate Techniques", *Second Edition, Academic Press*, 1202 pages, Part 3 of 12, 2008, pp. 158-259.
Hermanson, Greg, "Bioconjugate Techniques", *Second Edition, Academic Press*, 1202 pages, Part 4 of 12, 2008, pp. 260-361.
Hermanson, Greg, "Bioconjugate Techniques", *Second Edition, Academic Press*, 1202 pages, Part 5 of 12, 2008, pp. 362-463.
Hermanson, Greg, "Bioconjugate Techniques", *Second Edition, Academic Press*, 1202 pages, Part 6 of 12, 2008, pp. 464-565.
Hermanson, Greg, "Bioconjugate Techniques", *Second Edition, Academic Press*, 1202 pages, Part 7 of 12, 2008, pp. 566-667.
Hermanson, Greg, "Bioconjugate Techniques", *Second Edition, Academic Press*, 1202 pages, Part 9 of 12, 2008, pp. 770-871.
Hermanson, Greg, "Bioconjugate Techniques", *Second Edition, Academic Press*, 1202 pages, Part 1 of 12, 2008, pp. 1-105.
Merkus, Henk, "Particle Size Measurements", *Springer, ISBN 978-1-4020-9015-8*, 2009.
PCT/US2014/064691 "International Search Report and Written Opinion of the International Searching Authority", dated Feb. 27, 2015, 11 pages.
Rubinstein, M. et al., "Polymer Physics", *Oxford University Press, ISBN-13: 978-0198520597*, 2003.
Sambrook, et al., "Molecular Cloning: A Laboratory Manual", *3rd Ed., Ch. 8 Cold Spring Harbor Laboratory Press, N.Y.*, 128 pages, Part 1 of 5, 2001, pp. 8.1-8.23.
Sambrook, et al., "Molecular Cloning: A Laboratory Manual", *3rd Ed., Ch. 8 Cold Spring Harbor Laboratory Press, N.Y.*, 128 pages, Part 2 of 5, 2001, pp. 8.24-8.49.
Sambrook, et al., "Molecular Cloning: A Laboratory Manual", *3rd Ed., Ch. 8 Cold Spring Harbor Laboratory Press, N.Y.*, 128 pages, Part 3 of 5, 2001, pp. 8.50-8.75.
Sambrook, et al., "Molecular Cloning: A Laboratory Manual", *3rd Ed., Ch. 8 Cold Spring Harbor Laboratory Press, N.Y.*, 128 pages, Part 4 of 5, 2001, pp. 8.76-8.101.
Sambrook, et al., "Molecular Cloning: A Laboratory Manual", *3rd Ed., Ch. 8 Cold Spring Harbor Laboratory Press, N.Y.*, 128 pages, Part 5 of 5, 2001, pp. 8.102-8.126.

* cited by examiner

ROTOR PLATE AND BUCKET ASSEMBLY AND METHOD FOR USING SAME

CROSS-REFERENCE TO RELATED APPLICATION(S)

This application claims benefit of U.S. Provisional Application No. 61/902,724, filed Nov. 11, 2013, which is incorporated herein by reference in its entirety.

This application claims benefit of U.S. Provisional Application No. 61/934,271, filed Jan. 31, 2014, which is incorporated herein by reference in its entirety.

FIELD OF THE DISCLOSURE

This disclosure, in general, relates to rotor assemblies and methods for using such rotator assemblies.

BACKGROUND

In fields such as chemistry, molecular biology, and biomedical sciences, researchers increasingly rely on small-scale sensor arrays for conducting testing. In particular, analytes, particularly analytes attached to beads or particle substrates, are deposited onto the small-scale sensor arrays for testing. As the number of sensors increases and the size of the individual sensors in the sensor array decreases, depositing analytes into the sensor array is increasingly difficult. Factors such as Brownian motion become increasingly dominant over gravity.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an exemplary embodiment, the rotor assembly is configured to rotate around a central axis and includes a rotor plate configured to hold one or more buckets. The buckets can secure a sensor array component. In addition, the rotor plate is rotatably attached or coupled to the buckets in a manner that allows rotation of the buckets around an axis extending in a direction of rotation of the rotor assembly. In addition, the rotor assembly can include a stop plate that is rotatable relative to the rotor plate between an open position and a closed position. In an open position, the buckets can rotate around the axis extending along a path of rotation of the rotor assembly. In a closed position, the stop plate engages the buckets, preventing them from rotating. The buckets may be weighted so that when the rotary assembly is rotating, the buckets can rotate to a desired angle around an axis extending along a direction of rotation and relative to a plane of rotation of the rotor assembly. The stop plate can further include a ring to engage a tip of a pipetting robot. The pipetting robot can engage the ring to allow rotation of the stop plate relative to the rotor plate so that the stop plate can be moved between the open position and the closed position.

In a further exemplary embodiment, the stop plate of the rotor assembly can be positioned in a closed position, securing the buckets in a loading position that prevent the buckets from rotating out of the plane of rotation of the rotor assembly. A sensor array assembly can be inserted into the buckets and a solution can be applied to the sensor array assembly. The stop plate can be moved into an open position allowing rotation of the buckets during spinning of the rotor assembly. Subsequently, the stop plate can be moved back into a closed position, securing the bucket and limiting rotation of the bucket. The bucket and sensor array assembly can be spun again while the bucket is secured and unable to rotate around an axis extending in a direction of rotation of the rotor assembly. Subsequently, the remaining solution can be removed from the sensor array assembly, and the sensor array assembly can removed from the bucket and placed into a testing system.

Figure 1:
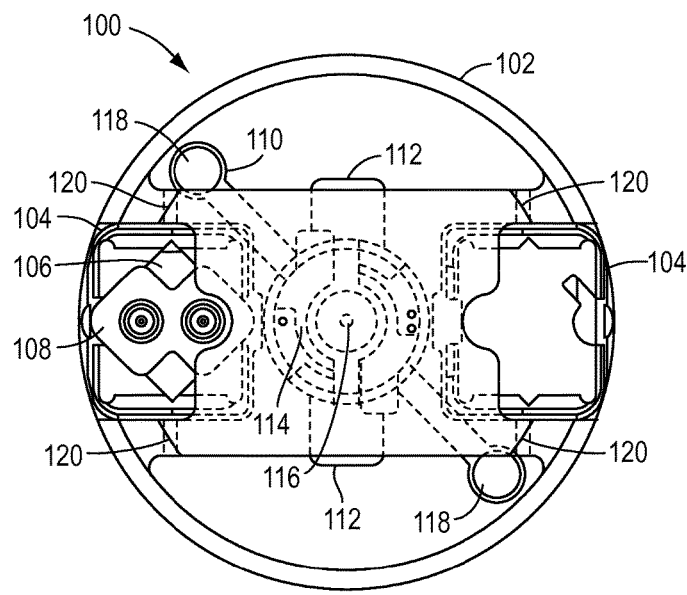
FIGS. 1 and 2 include illustrations of a plan view of an exemplary rotor assembly, a plane of rotation of the rotor assembly being in the plane of the plan view depicted.
Figure 2:
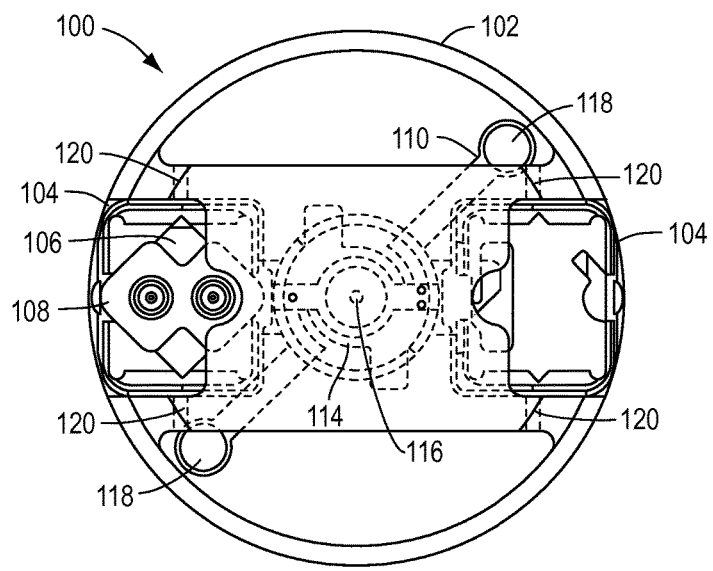

In an exemplary embodiment illustrated in FIG. 1 and FIG. 2, a rotor assembly 100 can rotate or spin around a central axis 116. In an example, the rotor assembly 100 can includes a rotor plate 102, which includes axles 120 to engage one or more buckets 104. In the illustrated example, the rotor plate 102 is configured to receive two buckets 104. Alternatively, the rotor assembly and rotor plate 102 can be configured to receive at least one bucket, such as at least two buckets, at least four buckets, or at least six buckets, but not greater than 20 buckets. The buckets 104 are configured to receive a sensor array component 106 and an associated cap 108. The cap 108 can assist with supplying a solution to or retrieving a solution from the sensor array component 106.

The rotor assembly 100 can further include a stop plate 110. The stop plate 110 can include wings 112 to engage the buckets 104, limiting rotation of the buckets around axles 120. The stop plate 110 can further include rings 118 that can be engaged, for example, by a tip of a pipetting robot. Using a pipetting robot and optionally the associated centrifuge motor, the stop plate 110 can be rotated around the central axis 116 or relative to the rotor plate 102, moving the wings 112 from an open position as illustrated in FIG. 1 to a closed position as illustrated in FIG. 2 in which the wings 112 engage the buckets 104 and limit the rotation the buckets 104 around the axels 120.

In addition, the rotor assembly 100 can include a coupler 114 to secure the rotor assembly 100 to the central axis 116 of a centrifuge motor.

Figure 3:
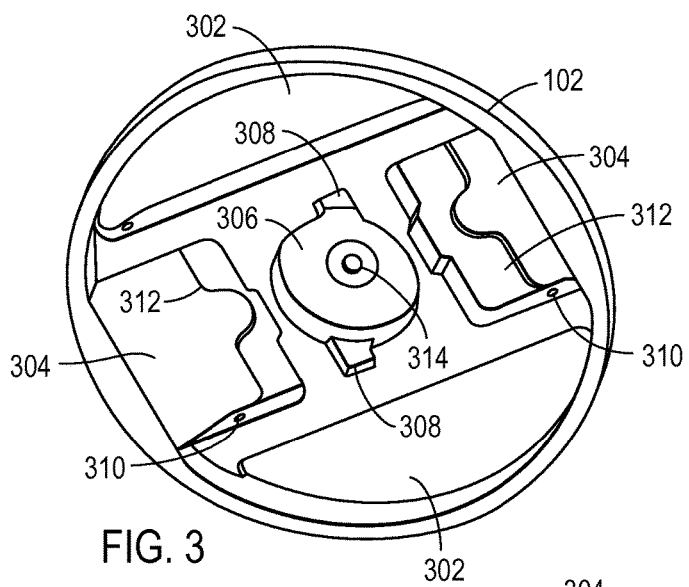
FIGS. 3, 4, and 5 include illustrations of an exemplary rotor plate.
Figure 4:
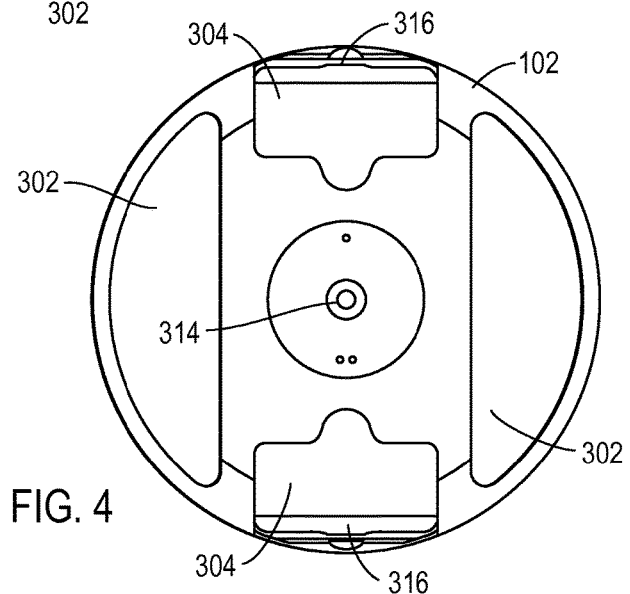
Figure 5:
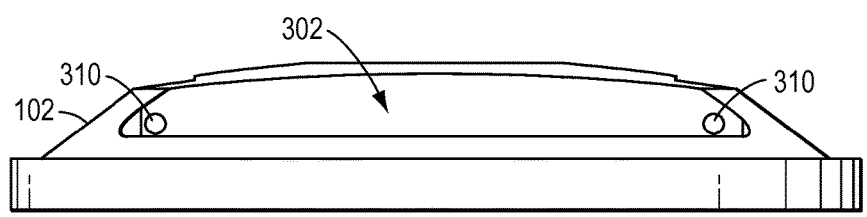

As illustrated in FIG. 3, FIG. 4, and FIG. 5, an exemplary rotor plate 102 includes openings 304 to receive buckets 104. In particular, the rotor plate 102 includes recesses 310 to receive axles 120 that are to engage the buckets 104 (illustrated in FIG. 1 and FIG. 2). The axles 120 can extend into the openings 304 and engage buckets. The rotor plate 102 also includes openings 302 through which stop plate rings 118 (illustrated in FIG. 1 and FIG. 2) can be engaged, for example, by a pipetting robot. The rotor plate 102 includes a central recess 306 to engage the stop plate 110 and the coupler 114 (illustrated in FIG. 1 and FIG. 2). Optionally, the central recess 306 can include slots 308 to engage wings (e.g., wings 1012 illustrated in FIG. 9 and FIG. 10) of a coupler 114 and limit relative motion of the coupler 114 and the rotor plate 102 (illustrated in FIG. 1 and FIG. 2). In particular, when the coupler 114 is rotated, the wings sufficiently engage the slots 308 and cause the rotor plate 102 to move with the coupler 114 with limited play. The rotor plate 102 can also include a central bore 314 to receive the fitting.

In proximity to the bucket opening 304 of the rotor plate 102, the rotor plate 102 can include an upper stop surface 312 and a rear stop surface 316. When a stop plate 110 is in a closed position, the stop plate 102 can force a bucket 104 or sensor array assembly into contact with the upper stop surface 312 or the backstop surface 316, limiting rotation of the bucket around the axles 120 engaging the recesses 310.

Figure 6:
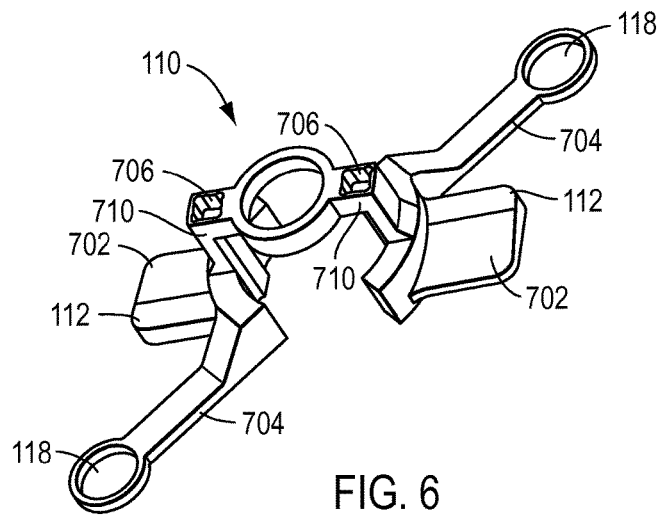
FIGS. 6, 7, and 8 include illustrations of an exemplary stop plate.
Figure 7:
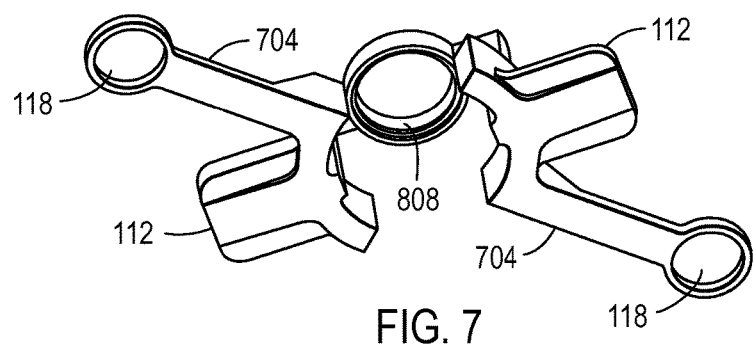
Figure 8:
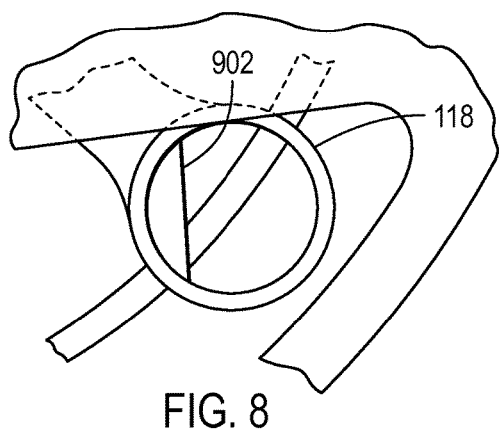

FIG. 6, FIG. 7, and FIG. 8 include illustrations of an exemplary stop plate 110. The stop plate 110 can engage a coupler 114 and a rotor plate 102 such that the stop plate 110 is rotatable relative to the rotor plate 102 and coupler 114 (illustrated in FIG. 1 and FIG. 2). The stop plate 110 includes wings 112 to engage buckets 104 when in a closed position. In a particular example, the wings 112 included a chamfered surface 702 that engages the buckets 104 when the stop plate 110 is closing and pushes the buckets into the closed position. The stop plate 110 can further include a central opening 808 to engage a central shaft of the coupler 114.

Further, the stop plate 110 includes arms 704 and distal rings 118. The rings 118 can be engaged to permit relative rotation of the stop plate 110 around the axis 116 relative to the coupler 114 and rotor plate 102 (illustrated in FIG. 1 and FIG. 2). Optionally, the stop plate 110 includes stop surfaces 710 that engage stop surfaces (e.g., stop surfaces 1004 of FIG. 9 and FIG. 10) of the coupler 114 when moved between the open and closed positions. Further, the stop plate 110 can include recesses 706 to receive magnets. The magnets can assist with securing the stop plate 110 to the coupler 114 and maintain the stop plate 110 in a position during spinning of the rotor assembly. In particular, the coupler 114 or the rotor plate 102 can include complementary magnets that provide an attractive force when the stop plate 110 is in the closed or open position. When the stop plate 110 is in the closed or open positions and the ring 118 of the stop plate 110 is not engaged, the stop plate 110 spins around the central axis with the rotor plate 102 and the coupler 114.

As illustrated in FIG. 8, the distal ring 118 can be partially filled with a chamfered slip 902. The chamfered slip 902 can be configured to allow a tip to hold the stop plate 110 while the rotor assembly rotates, bringing the stop plate to a 90° position relative to its starting position, moving the stop plate 110 from an open position to close position or vice versa.

Figure 9:
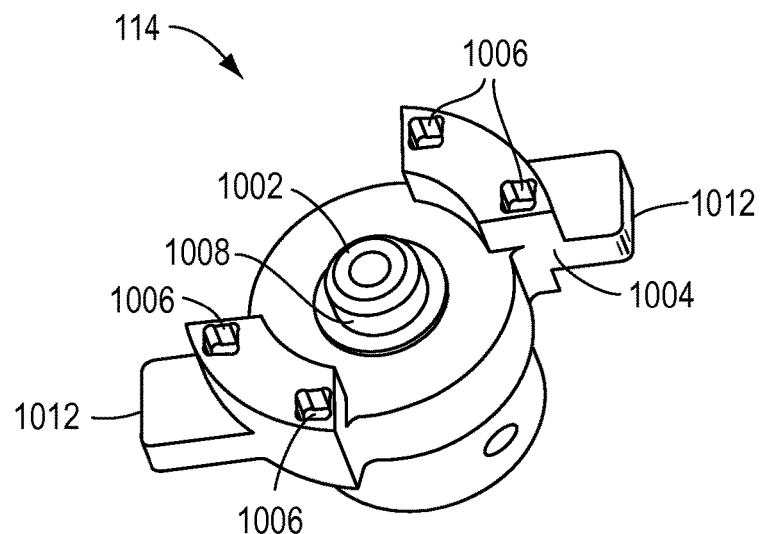
FIGS. 9 and 10 include illustrations of an exemplary coupler.
Figure 10:
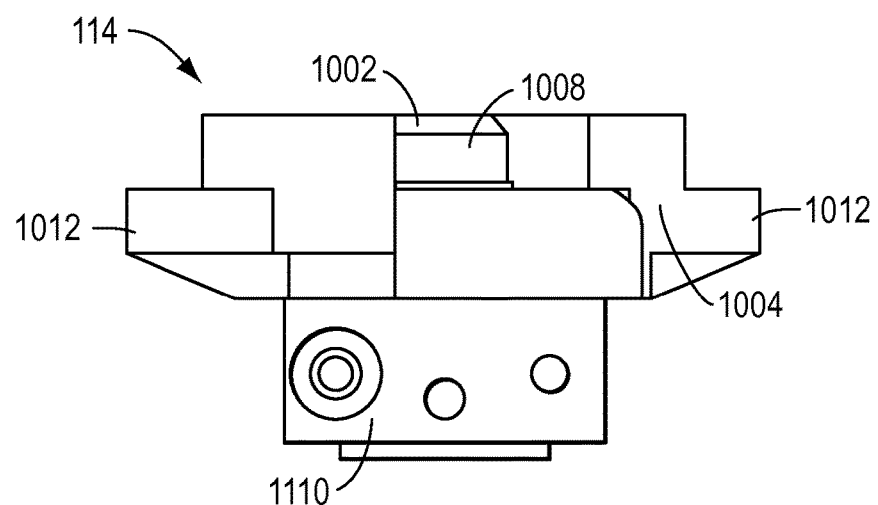

FIG. 9 and FIG. 10 include illustrations of an exemplary coupler 114. The coupler 114 can include wings 1012 to engage slots 308 of a rotor plate 102, as illustrated in FIG. 3. When engaged with the rotor plate 102, the wings 1012 limit the movement of the rotor plate 102 relative to the coupler 114. The coupler 114 can further include a central shaft chamfer 1002 for engaging a bearing of a rotor plate 102 and can include a contact surface 1008 for engaging a stop plate 110. When the stop plate 110 is rotated from an open to a closed position and back, the stop plate 110 can include a stop surface 710 that engages the stop surface 1004 of the coupler 114. In addition, the coupler 114 can include recesses 1006 to receive magnets that can secure the stop plate 110 in a desired position through attraction to magnets of the stop plate 110. As illustrated in FIG. 10, the coupler 114 can further include a motor shaft coupling 1110 to couple the coupler 114 and rotor assembly 100 to the motor shaft of a centrifuge motor.

Figure 11:
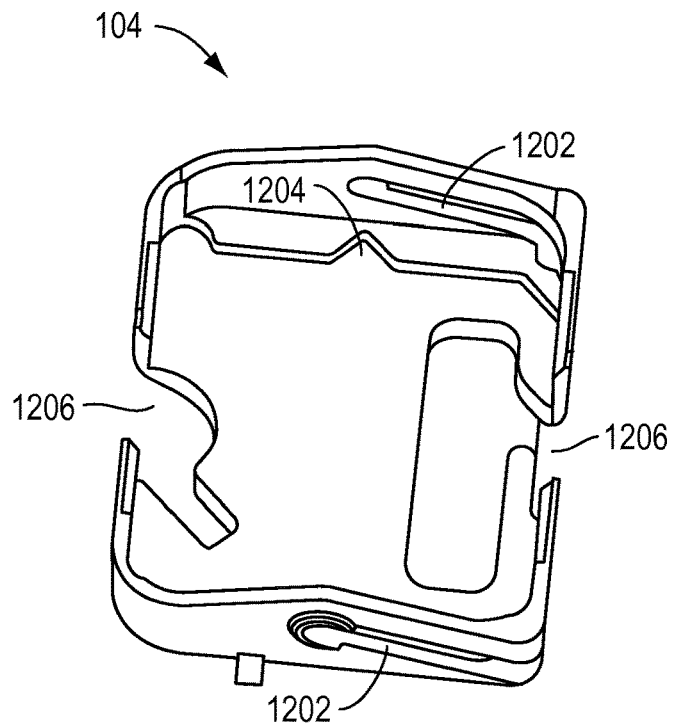
FIGS. 11 and 12 include illustrations of an exemplary bucket.
Figure 12:
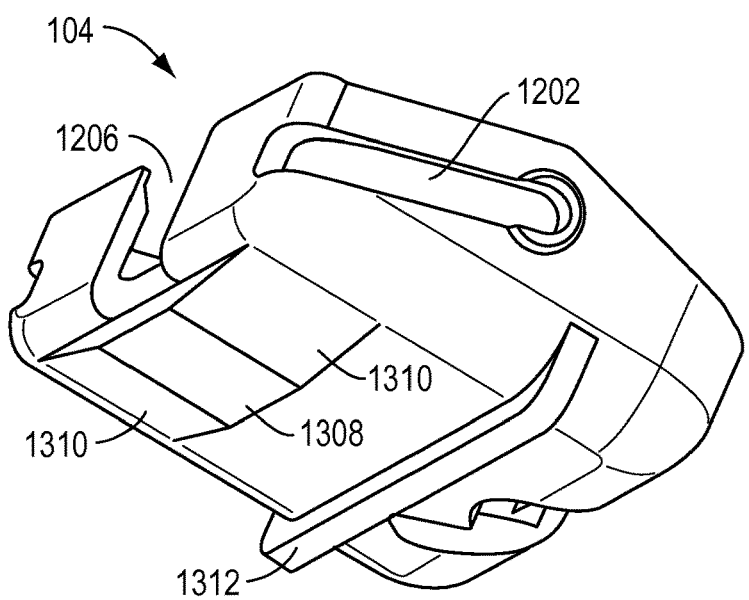

FIG. 11 and FIG. 12 include illustrations of an exemplary bucket 104. The exemplary bucket 104 includes channels 1202 to slidably engage axles 120 attached to a rotor plate 102. The bucket 104 can further include a patterned surface 1204 to engage a sensor array component. Openings 1206 can be provided to further secure the sensor array assembly or accommodate protruding edges of the sensor array assembly.

At a bottom surface of the bucket 104, as illustrated in FIG. 12, a stop surface 1308 can be positioned between chamfered surfaces 1310. When the stop plate 110 is moved into a closed position, the chamfered surface 702 of the wings 112 of the stop plate 110 engage the chamfered surface 1310 of the bucket 104, moving the bucket 104 into a position that secures the bucket 104 and limits rotation of the bucket 104. Further, the bucket 104 can include a rail or other feature 1312 that permits the bucket 104 to sit flat on a desktop surface when the bucket 104 is not engaged with the rotor assembly 100.

Figure 13:
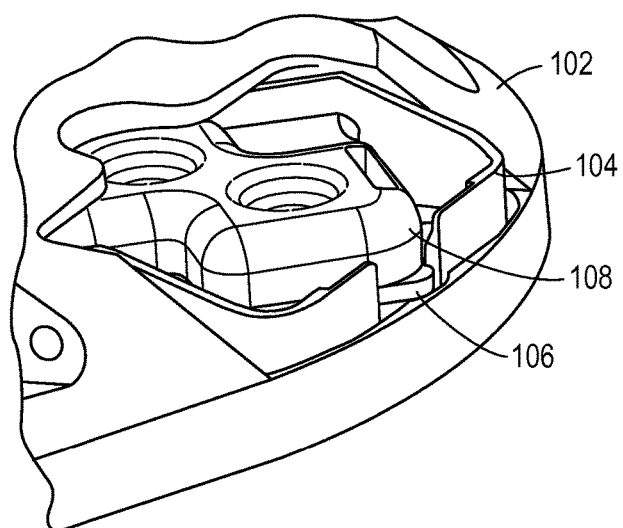
FIGS. 13 and 14 include illustrations of a portion of an exemplary rotor assembly.
Figure 14:
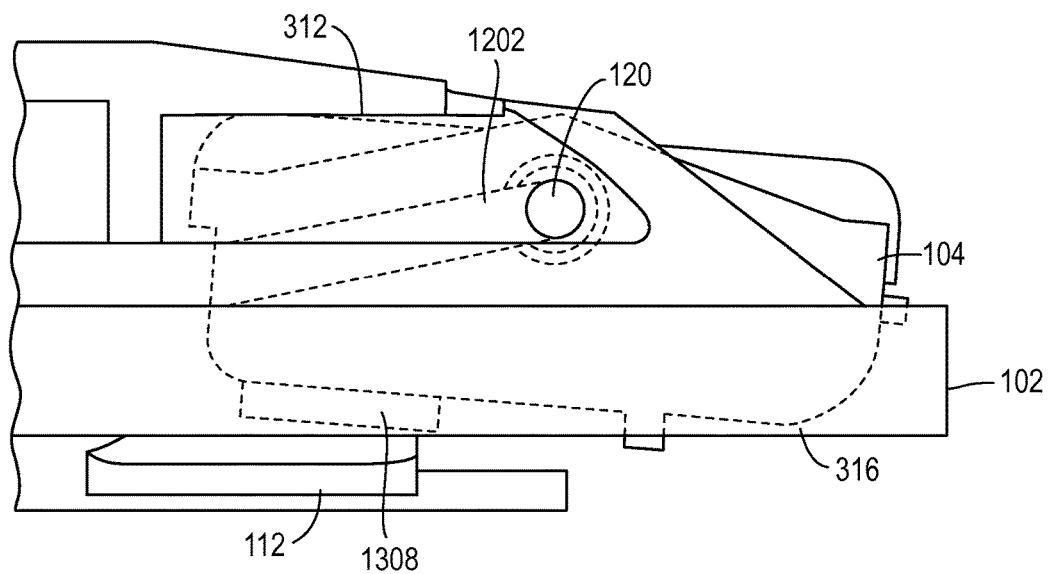

In particular, as illustrated in FIGS. 13 and 14, the bucket 104 can be slid into position in the rotor plate 102, engaging axles 120 along channels 1202. When the sensor array assembly 106 including the cap 108 is inserted into the bucket 104 and the wing 112 of the stop plate 110 engages the stop surface 1308 of the bucket 104, the bucket 104 is secured against a top stop surface 312 or against a rear stop surface 316 of the rotor plate 102. Accordingly, when in a position of the bucket received in the opening and the stop plate in the closed position, the bucket is held in position to lie between a bottom surface of the rotor plate and a top surface of the rotor plate. As illustrated, the bucket 104 can have a horizontal or negative angle relative to the plane of rotation of the rotor assembly 100 when the stop plate is in the closed position. For example, the bucket 104 and associated sensor array assembly 106 can have an angle in a range of 5° to -15°, such as an angle of 5° to -10°, or even an angle of 0° to -5° relative to the plane of rotation of the rotor assembly when the stop plate is in the closed position. Herein, positive angles indicate that the top of the sensor array assembly or bucket 104 tilt to face the central axis of the rotor assembly. When the stop plate 110 is in the open position, the bucket 104 can swing around axles 118. In particular, when the rotor assembly 100 is rotating around the central axis 116, the bucket 104 may be weighted to have an angle of at least 45°, such as at least 75°, or even at least 80° during spinning of the rotor assembly 100. During spinning of the rotor assembly 100, the bucket 104 may swing to a position or angle in a range of 85° to 110°, such as an angle of 85° to 105°, or even an angle of 85° to 95°, such as approximately 90°, relative to the plane of rotation of the rotor assembly 100.

Figure 15:
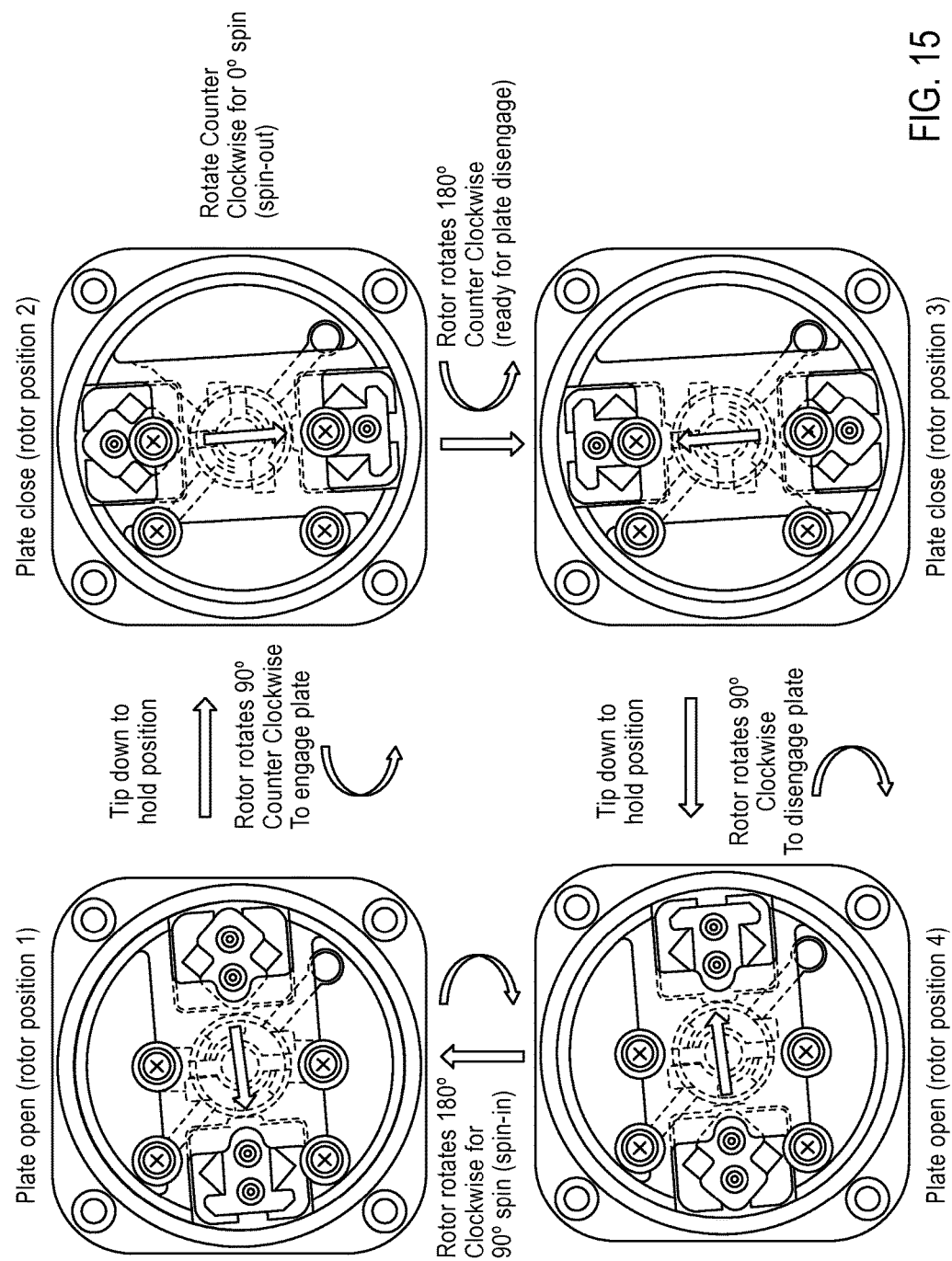
FIG. 15 includes an illustration of an exemplary rotor assembly.

To further illustrate the operation of the rotor assembly, FIG. 15 shows the rotor in an open position at rotor position 1. A tip can engage a ring of the stop plate, and the rotor plate can be rotated 90°, for example counterclockwise, to engage the rotor plate and buckets in the closed rotor position 2. To open the stop plate, the rotor assembly can be rotated 90° counter clockwise to rotor position 3. A tip can be applied into a ring of the stop plate, and the rotor plate can rotate 90° clockwise to disengage the stop plate and move into open rotor position 4. The rotor assembly can further be rotated 180° clockwise to begin the process of closing and opening the rotor assembly again.

Figure 16:
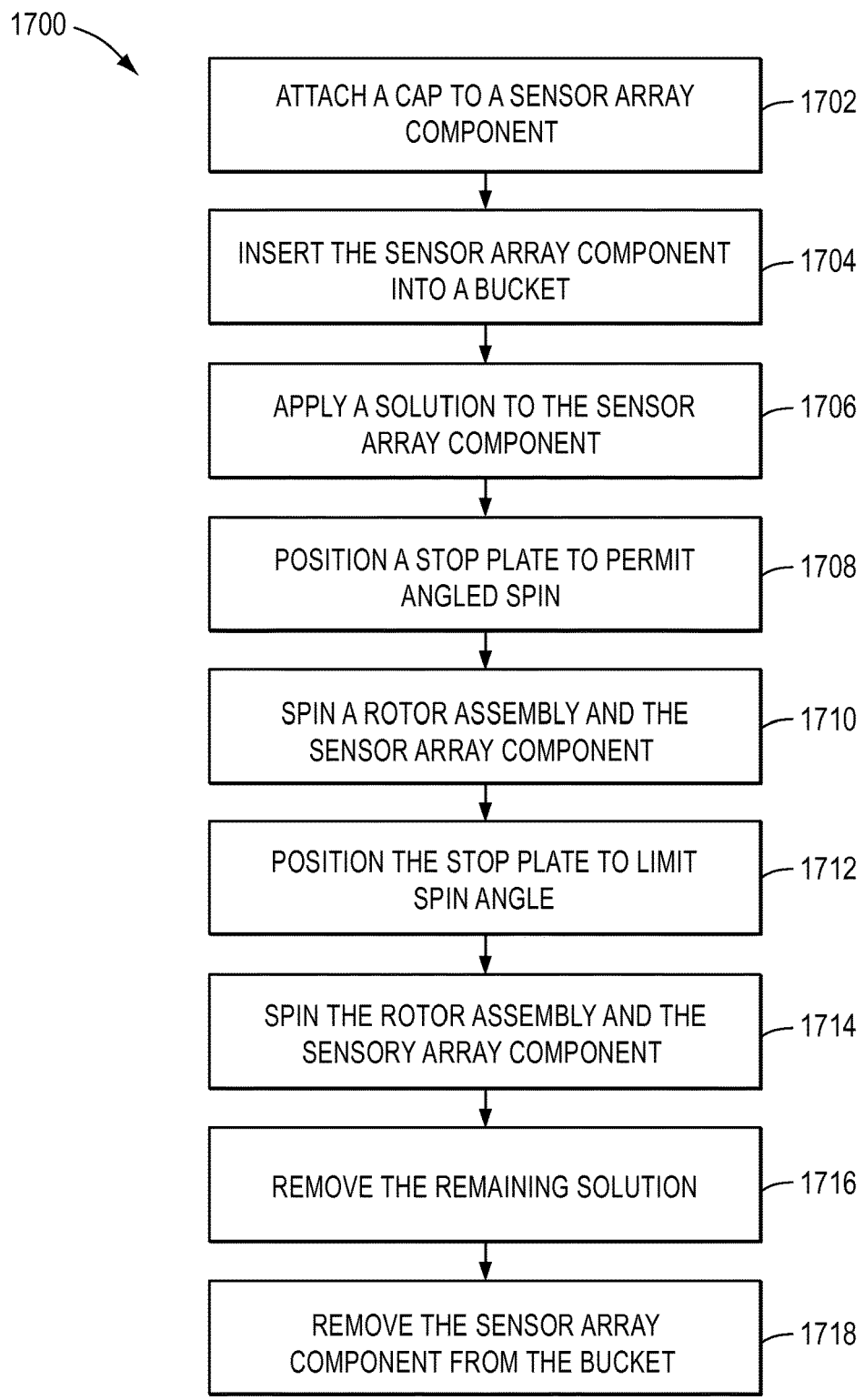
FIGS. 16 and 17 include illustrations of block flow diagrams of exemplary methods for using a centrifuge including an exemplary rotor assembly.

In particular, the rotor assembly can be used to load samples onto a sensor array. As illustrated in FIG. 16, a method 1700 optionally includes attaching a cap to a sensor assembly, as illustrated at 1702. In particular, the cap can provide easier access for pipetting solutions into and out of the sensor array.

The sensor array assembly is inserted into a bucket, as illustrated at 1704. In particular, the bucket secures the sensor array assembly when the rotator assembly spins.

Optionally, the bucket is inserted into the rotor assembly, and a solution is applied to the sensor array, as illustrated at 1706. In particular, the solution can be applied while the stop plate is in the closed position to hold the bucket in place. Alternatively, the solution can be applied prior to inserting the bucket into the rotor plate.

As illustrated at 1708, the stop plate can be positioned to an open position that permits the bucket and sensor array assembly to swing relative to an axis extending in the direction of the rotation of the rotary assembly. In particular, the bucket can be weighted to rotate to a positive angle around an axis that extends in a direction along a direction of rotation of the rotor assembly.

Once the stop plate has been moved into an open position, the rotor assembly including the bucket and sensor array assembly can be spun, as illustrated at 1710. As a result, the bucket and sensor array assembly can rotate to an angle of at least 45°, such as at least 75°, or even at least 80° during spinning of the rotor assembly. During spinning of the rotor assembly, the bucket may swing to a position or angle in a range of 85° to 110°, such as an angle of 85° to 105°, or even an angle of 85° to 95°, such as approximately 90°, relative to the plane of rotation of the rotor assembly.

Following spinning, the stop plate can be positioned into a closed position to limit the spin angle of the bucket and sensor array assembly, as illustrated at 1712. For example, the stop plate can limit the spin angle of the bucket to near zero or slightly negative. Optionally, the rotary assembly and the sensor array assembly can be spun, as illustrated at 1714, while the stop plate is in the closed position and limits the movement of bucket. In particular, spinning at a negative angle can facilitate removal of solution from the sensor array assembly.

The remaining solution can be removed from the sensor array assembly, as illustrated at 1716, for example, by pipetting the remaining solution from a recess in the cap. The sensor array assembly can then be removed from the bucket as illustrated at 1718 and used in a separate testing apparatus.

Figure 17:
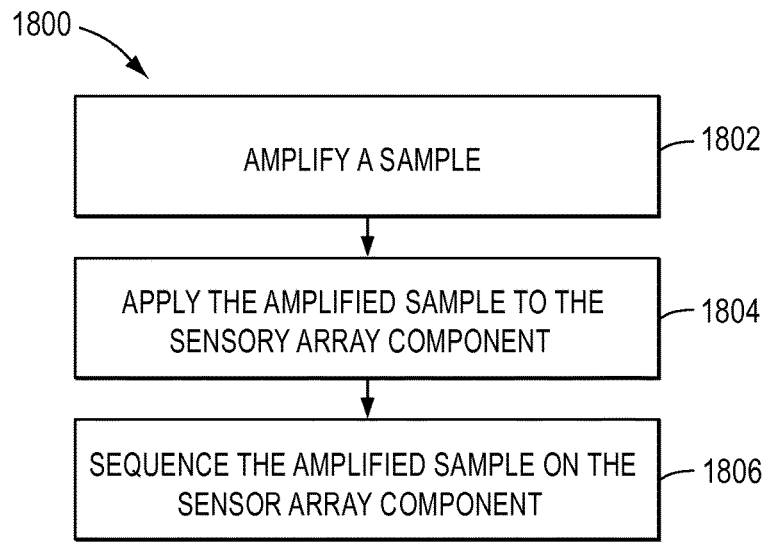

In a particular example, the sensor array assembly has particular use when sequencing target polynucleotides. As illustrated in the method 1800 of FIG. 17, a polynucleotide sample can be amplified, as illustrated at 1802. In particular, the sample can be amplified on bead or particulate substrates.

As illustrated at 1804, the amplified sample, particularly beads or particle substrates, can be applied to a sensor array component. In particular, a solution including the amplified sample is applied to or loaded into the sensor array component, and undergoes spinning under various angular conditions, securing to the bead or particulate substrates into the sensor array component. The sensor array component can then be inserted into a sequencing apparatus and the amplified sample that is loaded onto the sensor array component can be sequenced, as illustrated at 1806.

Figure 18:
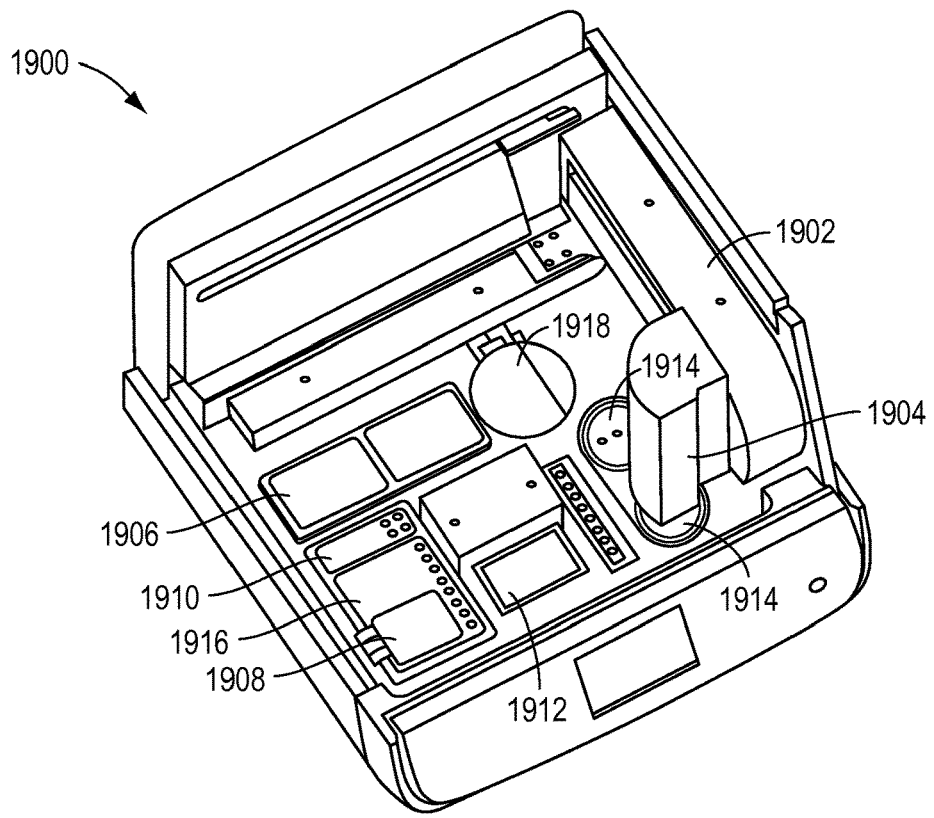
FIG. 18 includes an illustration of an exemplary pipetting robot.

Such a rotor assembly finds particular use in a pipetting robot assembly. FIG. 18 illustrates an exemplary configuration. The system 1900 includes a translation device, such as a xyz-robot 1902 operable to move a syringe pump 1904 over ranges of three orthogonal axes. The system 1900 further includes a tip rack 1906 for storing pipette tips useful by the syringe pump 1904. The system 1900 can also include a tube rack 1916 that can store empty tubes or can store strips of reagent tubes, such as reagent strip 1908. In a further example, the system 1900 can include a chilled block 1910 for storing temperature sensitive reagents, such as enzymes. The system 1900 can further include a thermocycler 1912, one or more emulsion breaking centrifuges 1914, and a bead loading centrifuge 1918 with motor. In particular, the bead loading centrifuge 1918 can include a rotor assembly, such as an embodiment of the rotor assembly described above. The system 1900 can further include an optical sensor or a tip removal device.

In operation, the translation device 1902 manipulates the position of the syringe pump 1904 to retrieve tips from the tip rack 1906 and perform the various functions of the system 1900. For example, the syringe pump 1904 can be utilized along with reagents of the reagent rack 1916 to form an emulsion including enzymes and a sample in an aqueous discontinuous phase surrounded by an immiscible continuous phase. For example, the sample and enzyme solutions can be stored in the chilled reagent block 1910. The emulsion can be formed within a tube in the reagent rack 1916. In particular, the emulsion can be generated by rapid pipetting. In another example, the emulsion can be generated by pipetting through a restriction.

Following formation of the emulsion, the emulsion can be transferred to a thermocycler plate on a thermocycler 1912 using the translation device 1902 and the syringe pump 1904. The thermocycler plate 1912 can be utilized to perform polymerase chain reaction (PCR) or recombinase polymerase amplification (RPA). Upon completion of the PCR reaction, the emulsion can be transferred from the thermocycler 1912 to one of the emulsion breaking centrifuges 1914. The emulsion can be injected into the emulsion breaking centrifuge 1914 that includes tubes having a surfactant solution. As the centrifuge rotates, the emulsion is injected into the centrifuge. When the emulsion contacts the surfactant solution within the tubes of the centrifuge 1914, aqueous phase components are driven into the solution while oil phase components are removed from the tube.

The PCR or RPA process can generate amplified beads including a number of target polynucleotides. Such amplified beads can be washed and separated from other aqueous solution components using an enrichment system. In particular, the reagent rack 1916 can be modified with the magnet system to permit enrichment using magnetic particles that bind to the amplified beads.

Following enrichment, the beads can be transferred and loaded onto a sequencing device, such as a chip configured for detecting sequencing byproducts, using the loading centrifuge 1918. For example, aliquots of the solution including the amplified beads can be injected into ports on the sequencing device disposed on the rack within the loading centrifuge 1918. The centrifuge 1918 can be positioned and spun, for example, as described above, to facilitate the loading. In particular, a tip attached to the syringe pump 1904 can be positioned in a ring of a stop plate to move the stop plate between open and closed positions. The process can be repeated one or more times to improve loading density. As a result, a sequencing device loaded with amplified particles, incorporating amplified target nucleotides from the sample, is provided with minimal human interaction.

Throughout the process, the syringe pump 1914 can utilize a variety of pipette tips acquired from the pipette tip rack 1906. Further, tips can be provided that assist with movement of magnets, loading of tubes within the emulsion breaking centrifuge 1914, configuring the loading centrifuge, or other functions. To assist with removal of the tips from the syringe pump 1904, a tip removal device can be provided.

In other embodiments, the stop plate can be formed from two separate components, the magnets can be positioned at different locations on different components, and the axles of the buckets can be secured to the buckets and be of different sizes in contrast to securing the axles to the rotor plate. While exemplary embodiments are illustrated in FIG. 19-FIG. 26, the illustrated features can be interchangeable between embodiments.

Figure 19:
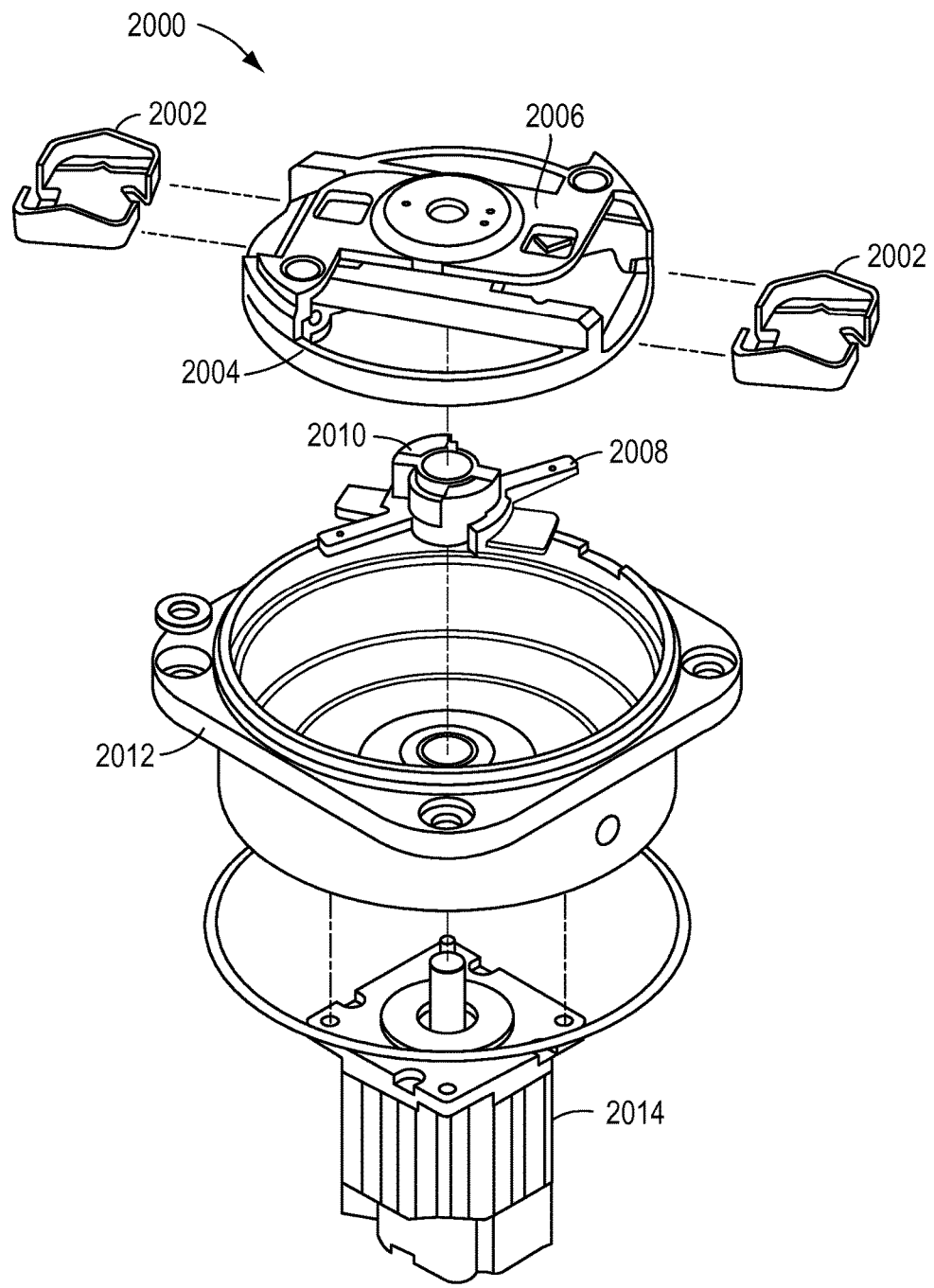
FIG. 19 includes an illustration of a centrifuge assembly.

As illustrated in FIG. 19, a centrifuge 2000 includes a bucket 2002 that can be secured in a rotor plate 2004. An upper stop plate 2006 is positioned coaxially with the rotor plate 2004. The upper stop plate 2006 can be coupled to a lower stop plate 2008, which includes wings to engage the buckets 2002. The rotor plate 2004 is secured to a coupler 2010, which secures the rotor assembly to the shaft of a motor 2014. The upper stop plate 2006 and the lower stop plate 2008 can be rotatably secured to the coupler 2010. The rotor assembly can fit inside a casing 2012.

Figure 20:
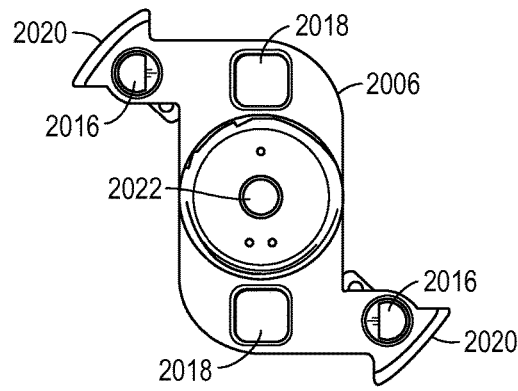
FIGS. 20, 21, and 22 include illustrations of exemplary upper stop plates.
Figure 21:
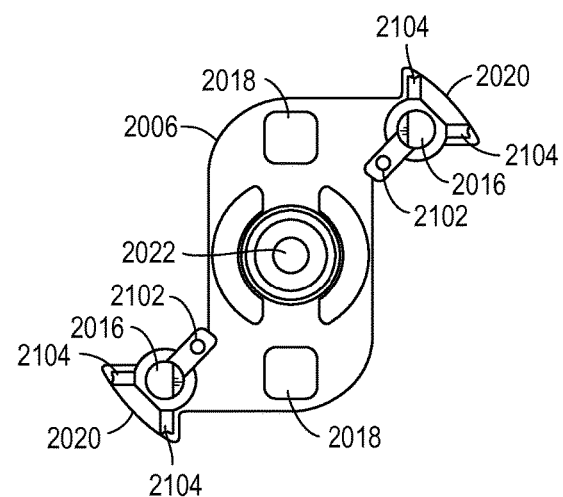
Figure 22:
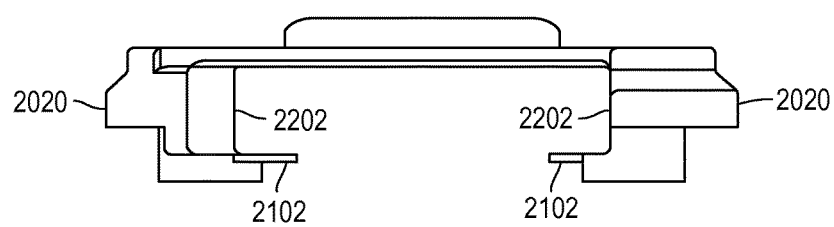

FIG. 20, FIG. 21, and FIG. 22 includes illustrations of an upper stop plate 2006. Similar to the stop plate described above, the upper stop plate 2006 includes openings 2016 to engage a robot, in particular a pipetting robot and allow rotation of the upper and lower stop plates relative to the rotor plate 2004. In addition, the upper stop plate 2006 can include a window 2018 that provides access to ports on devices within the buckets 2002, for example, when the upper stop plate 2006 and lower stop plate 2008 are engaged with the bucket 2002. The upper stop plate 2006 can also include a central bore 2022 to engage the coupler 2010. Edges of the upper stop plate 2006 can be configured with surfaces 2020 that correspond with an inner surface of a casing 2012.

As illustrated in the bottom view of the upper stop plate 2006 in FIG. 21, the upper stop plate 2006 can include a coupling arm 2102 to secure the upper stop plate 2006 to the lower stop plate 2008. The upper stop plate 2006 can also include magnets 2104 to engage magnets on the rotor plate 2004 to assist with holding the position of the upper stop plate 2006 and lower stop plate 2008 in the designated position. Alternatively, magnets can be positions on the lower stop plate 2008.

As illustrated in the side view in FIG. 22, the upper stop plate 2006 can include extensions 2202 terminating in the coupling structures 2102 to engage the lower stop plate 2008. Alternatively, the lower stop plate 2008 can include the extension and coupling structure to engage the upper stop plate 2006. Using such a configuration, the upper stop plate 2006 can reside above the rotor plate 2004, and the lower stop plate 2008 can reside below the rotor plate 2004 relative to the axis of rotation of the rotor assembly.

Figure 23:
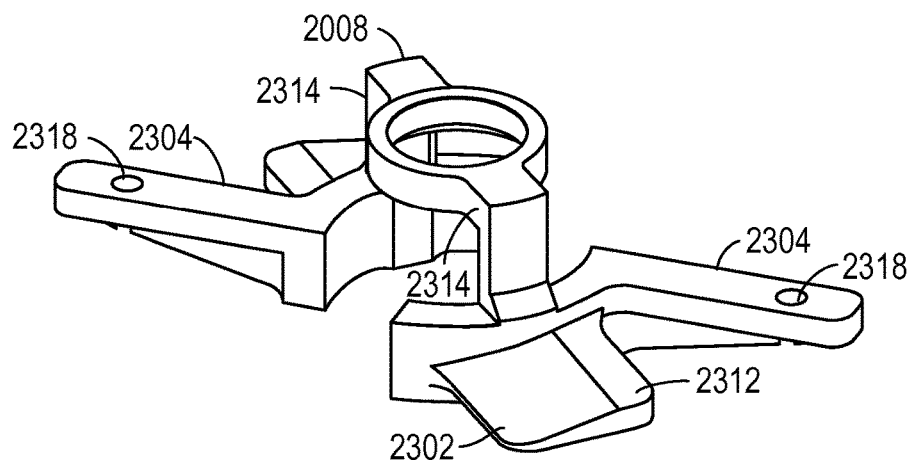
FIG. 23 includes an illustration of an exemplary lower stop plate.

FIG. 23 includes an illustration of the lower stop plate 2008. The lower stop plate includes wings 2302 to engage buckets 2002 disposed on the rotor plate 2004. The wings 2302 can include a horizontal planar surface 2312 that engages the buckets 2002 in a closed position, securing the buckets preventing their rotation. The lower stop plate 2008 can also include arms 2304 and coupling positions 2318 to engage the upper stop plate 2006. The lower stop plate 2008 can further include stop surfaces 2314 to engage stop surfaces on the coupler 2010.

Figure 24:
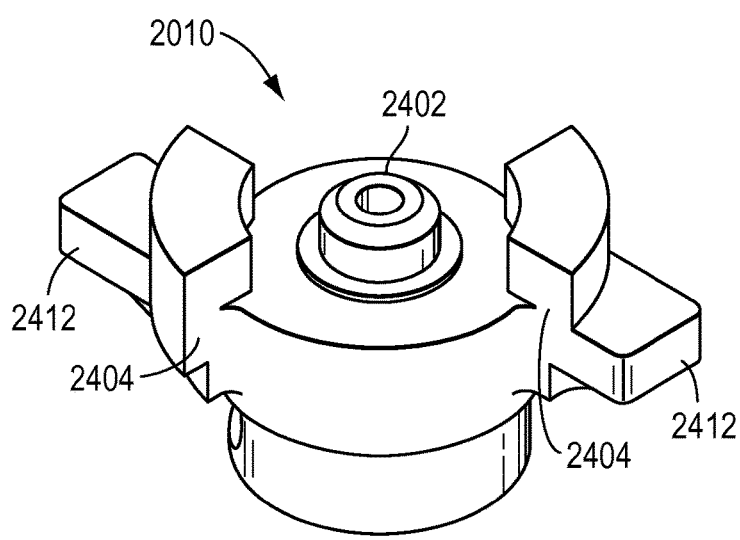
FIG. 24 includes an illustration of an exemplary coupler.
Figure 25:
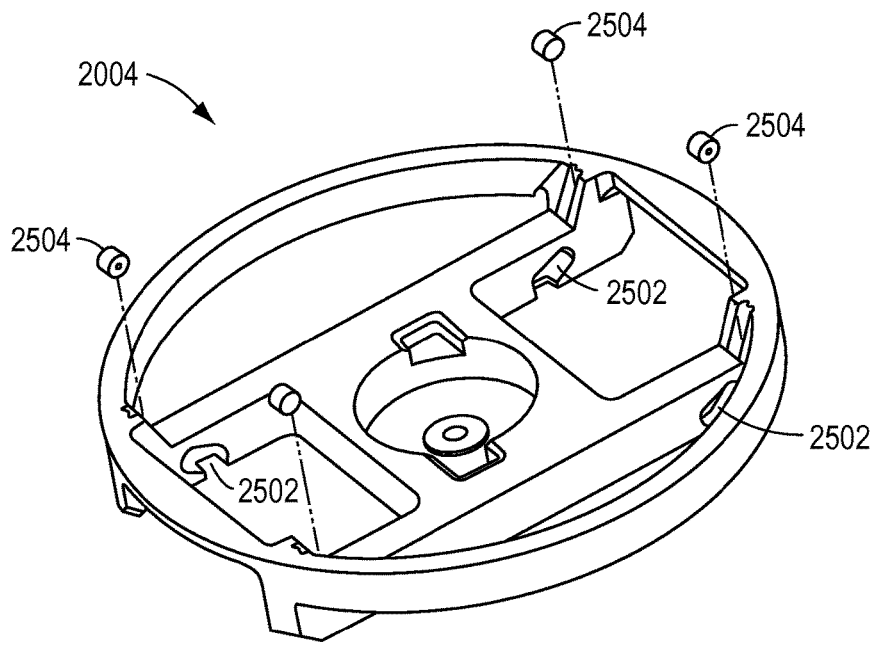
FIG. 25 includes an illustration of an exemplary rotor plate.

FIG. 24 illustrates a further exemplary embodiment of a coupler 2010. The coupler 2010 includes wings 2412 to engage the rotor plate 2004. In addition, the coupler 2010 includes a central shaft 2402 to engage the lower stop plate 2008, the rotor plate 2004, or the upper stop plate 2006. The upper stop plate 2006 and the lower stop plate 2008 engage the coupler 2010 in a manner that permits rotation relative to the coupler 2010. In particular, the upper stop plate 2006 or the lower stop plate 2008 when engaged to each other function similar to the stop plate described above and can moved between first and second positions, such as closed and open positions. The coupler 2010 includes stop surfaces 2404 that engage the stop surfaces 2314 of the lower stop plate 2008 when in one of the two positions.

The rotor plate 2004 includes features similar to those described in relation to the rotor plate above. In the illustrated example, the rotor plate includes embedded magnets 2504 that can engage magnets embedded within the upper stop plate 2006. In particular, the stop plate 2006 or 2008 can be held in an open or closed position through the interaction of the magnets when the rotor assembly is rotating about a central axis of the motor 2014.

Figure 26:
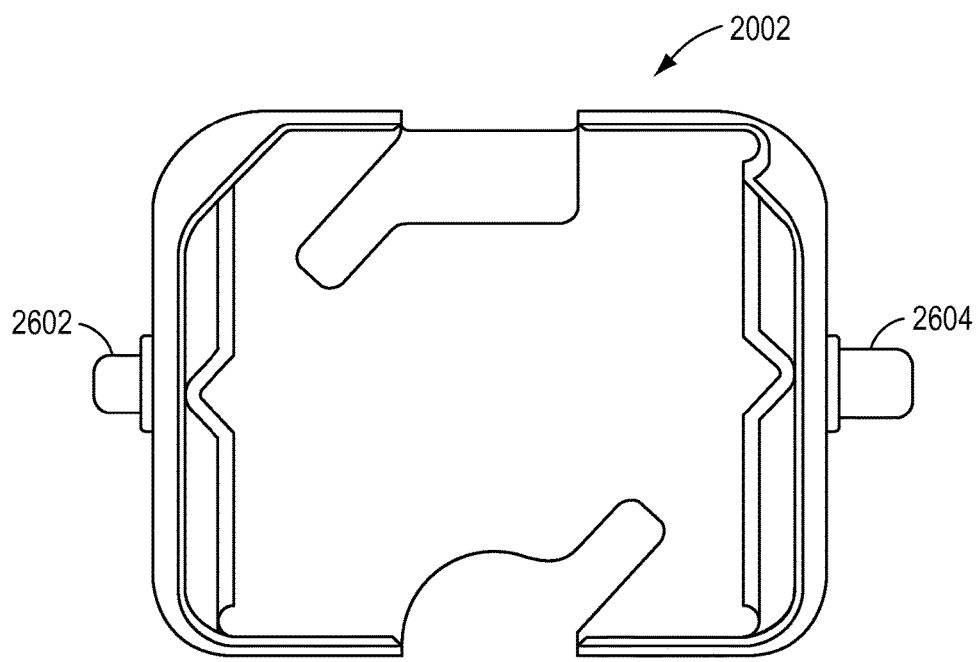
FIG. 26 includes an illustration of an exemplary bucket.

In further example, the rotor plate 2004 can include slots 2502 to receive axles of the buckets 2002. In such an example, the axles are secured to the buckets 2002 and can be slid into the slots 2502 to rotatably couple the buckets 2002 to the rotor plate 2004. In a particular example, the slots 2502 of the rotor plate 2004 can be configured to receive axles of different size. In particular, a slot 2502 on a clockwise side of the recess to receive the buckets 2002 can have a size different from the slots on the counterclockwise side. As illustrated in FIG. 26, the buckets 2002 can be configured with axles 2602 and 2604 of different diameter or different shape. As such, the buckets can engage the rotor plate 2004 in a single manner, preventing incorrect engagement of the buckets 2002 with the rotor plate 2004.

In a first aspect, a rotor assembly includes a rotor plate to rotate around a first axis; a bucket rotatably attached to the rotor plate and to rotate around a second axis; and a stop plate to rotate around the first axis relative to the rotor plate between an open position and a closed position, when in the closed position, the stop plate is to engage the bucket to fix an angular position of the bucket relative to a plane of rotation of the rotor assembly.

In an example of the first aspect, the stop plate includes a wing with a chamfered surface to engage a surface of the bucket when the stop plate is moving to the closed position. For example, the bucket includes a chamfered surface to engage the chamfered surface of the stop plate.

In another example of the first aspect and the above examples, the stop plate includes an arm and a ring. For example, the rotor plate includes an opening through which the ring of the stop plate can be accessed. In an example, the ring includes a chamfered slip.

In a further example of the first aspect and the above examples, the rotor assembly includes a coupler having a central shaft to engage the rotor plate and the stop plate. For example, the coupler includes a stop surface to engage a stop surface of the stop plate when the stop plate is in an open or closed position. In another example, the coupler includes a magnet to attract a magnet of the stop plate when the stop plate is in an open or closed position. In an additional example, the rotor plate includes a recess with slots to receive the coupling, wings of the coupling to engage the slots of the rotor plate.

In an additional example of the first aspect and the above examples, the rotor plate includes a top stop surface to engage the bucket or a sensor array assembly when the stop plate is in a closed position.

In another example of the first aspect and the above examples, the rotor plate includes a rear stop surface to engage the bucket when the stop plate is in a closed position.

In a further example of the first aspect and the above examples, the bucket is weighted to provide an angular position relative to a plane of rotation of the rotor assembly when the rotor assembly is spinning In a second aspect, a system includes a pipetting robot having three dimensions of movement; and a centrifuge including a rotor assembly of the first aspect or any one of the examples of the first aspect.

In a third aspect, a method of loading a sensor array assembly includes applying a solution to a sensor array assembly disposed in a bucket of a rotor assembly when a stop plate of the rotor assembly is in a closed position; moving the stop plate to an open position; spinning the rotor assembly, the bucket rotating to a positive angle relative to a plane of rotation of the rotor assembly; moving the stop plate to the closed position; and spinning the rotor assembly, the bucket rotating to a horizontal or negative angle relative to the plane of rotation of the rotor assembly.

In an example of the third aspect, the rotor assembly is a rotor assembly of the first aspect or any one of the examples of the first aspect.

In a fourth aspect, a method of configuring a rotor assembly includes inserting a tip into a ring of a stop plate of the rotor assembly, the tip preventing the stop plate from moving; rotating a rotor plate of the rotor assembly relative to the stop plate; and removing the tip from the ring.

In an example of the fourth aspect, the stop plate includes a wing to engage a bucket rotatably coupled to the rotor plate when the rotor plate is rotated.

In another example of the fourth aspect, the stop plate includes a wing to disengage from a bucket rotatably coupled to the rotor plate when the rotor plate is rotated.

In a further example of the fourth aspect and the above examples, the method further includes rotating the rotor assembly 180°; inserting the tip into the ring; and rotating the rotor plate 90° relative to the stop plate.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A rotor assembly comprising:
   a rotor plate configured to rotate around a first axis, the rotor plate comprising an opening positioned proximate a perimeter of the rotor plate and extending radially inward toward a center of the rotor plate;
   a bucket configured to be received in the opening and rotatably attached to the rotor plate to rotate around a second axis; and
   a stop plate configured to rotate relative to the rotor plate around the first axis between an open position and a closed position;
   wherein, in a position of the bucket received in the opening and the stop plate in the closed position, the bucket is held in position to lie between a bottom surface of the rotor plate and a top surface of the rotor plate.

2. The rotor assembly of claim 1, wherein in the closed position, the stop plate prevents rotation of the bucket around the second axis.

3. The rotor assembly of claim 2, wherein in an open position of the stop plate, the bucket is rotatable about the second axis.

4. The rotor assembly of claim 1, wherein the stop plate comprises an arm terminating in a ring configured to engage a pipette.

5. The rotor assembly of claim 1, wherein the bucket further comprises a surface feature configured to retain a sensor array.

6. The rotor assembly of claim 1, wherein the bucket further comprises channels configured to receive axles extending from the rotor plate, the second axis extending through the axles.

* * * * *